United States Patent [19]

Stahl et al.

[11] Patent Number: 4,484,012

[45] Date of Patent: Nov. 20, 1984

[54] PRODUCTION OF MANNITOL AND HIGHER MANNO-SACCHARIDE ALCOHOLS

[75] Inventors: Howard Stahl, Scarsdale; Renee Bayha, Ithaca; Charles V. Fulger, Millwood, all of N.Y.; Evan J. Turek, Paramus, N.J.

[73] Assignee: General Foods Corporation, White Plains, N.Y.

[21] Appl. No.: 584,692

[22] Filed: Feb. 29, 1984

[51] Int. Cl.³ .................. C07C 29/14; C07C 31/26; C07C 27/04; C07G 3/00
[52] U.S. Cl. .................................. 568/863; 127/36; 127/43; 127/44; 536/4.1; 536/18.5; 536/124; 568/852; 568/868
[58] Field of Search ............... 568/863; 536/18.5, 124; 127/36, 43, 44

[56] References Cited

U.S. PATENT DOCUMENTS

| | | | |
|---|---|---|---|
| 3,579,380 | 5/1971 | Friese | 568/863 |
| 4,137,395 | 1/1979 | Buckl et al. | 536/124 |
| 4,292,451 | 9/1981 | deBerardinis et al. | 568/863 |
| 4,445,938 | 5/1984 | Verwaerde et al. | 568/863 |

*Primary Examiner*—J. E. Evans
*Attorney, Agent, or Firm*—Sam D. Walker; Thomas R. Savoie; Daniel J. Donovan

[57] ABSTRACT

A method for hydrolyzing coffee extraction residue materials to produce manno-saccharides having a degree of polymerization from 1 to 10 and subsequently neutralizing and reducing said mixture of manno-saccharides to their corresponding alcohols. The coffee material, preferably spent coffee grounds from a commercial percolation system, is hydrolyzed in a Plug Flow tubular reactor in the presence of an acid catalyst, such as sulfuric acid. Depending on the time, temperature, pressure and catalyst concentration selected, manno-saccharides or mannose is produced. The manno-saccharides or mannose produced are separated from coffee residue material in the form of a syrup and neutralized with calcium hydroxide. The neutralized mixture of manno-saccharides or mannose is reduced to their corresponding alcohols or mannitol.

39 Claims, 3 Drawing Figures

% Sugar Yield (spent grounds dry weight) in Plug Flow Reactor

% Sugar Yield (spent grounds dry weight) in Plug Flow Reactor

%Mannose in Soluble Solids in Plug Flow Reactor

% Glucose in Soluble Solids in Plug Flow Reactor

PRODUCTION OF MANNITOL AND HIGHER MANNO-SACCHARIDE ALCOHOLS

TECHNICAL FIELD

The present invention relates to a method for producing alcohols such as mannitol from a coffee extraction residue material. More particularly, the invention involves hydrolyzing a coffee extraction residue material, to manno-saccharides having a degree of polymerization (DP) from 1 to 10 and subsequently reducing the manno-saccharides to their corresponding alcohols such as a mannitol or mixtures of higher manno-saccharide alcohols.

BACKGROUND ART

Conventionally, mannitol is produced by the catalytic hydrogenation of invert sugar, which is an approximately equimolar mixture of glucose and fructose. Mannitol is produced as a mixture of sorbitol and mannitol in aqueous solution. The yield of mannitol in this situation ranges from 24 to 26% by weight, based on total dry solids, when hydrogenation is carried out under neutral or mildly acidic conditions such as those disclosed in U.S. Pat. No. 2,759,024 by Kasehagen. This yield can be increased by carrying out at least part of the hydrogenation in alkaline conditions, as described in U.S. Pat. Nos. 3,329,729 by Brandner et al. and 3,763,246 to DeBerardinis or by appropriate choice of catalyst, as described in U.S. Pat. No. 3,705,199 to DeBerardinis, or both.

The above processes are plural stage processes in which alkaline hydrogenation is followed by acid hydrogenation. Alkaline agents for the alkaline hydrogenation stages of those processes are alkali metal hydroxides such as sodium hydroxide, and alkaline earth metal hydroxides such as lime. U.S. Pat. No. 3,329,729 also suggests the addition of calcium carbonate as a buffering agent in addition to lime. In the above references, mannitol yeild are as follows: U.S. Pat. No. 3,329,729 is 30 to 36%; No. 3,705,199 is 28 to 29%; No. 3,763,246 is 27 to 31%. In each case, the balance of the reaction product is mostly sorbitol.

U.S. Pat. No. 4,029,578 by Kruse, discloses a process for obtaining sorbitol/mannitol solution from glucose by first catalytically epimerizing glucose in an acidic aqueous solution containing at least 50% by weight of glucose to obtain an epimerizate of glucose and mannose, and then catalytically hydrogenating this epimerizate to obtain an aqueous solution of sorbitol and mannitol. Epimerization according to that process is carried out at elevated temperature in the presence of molybdenum ion, such as molybdic acid or an ion exchange resin in the molybdite form. Hydrogenation catalyst and conditions for hydrogenating the glucose/mannose epimerizate to a mixture of sorbitol and mannitol are known.

Although yields of mannitol can be enhanced by hydrogenating either glucose or invert sugar under alkaline conditions rather than under neutral or mildly acidic conditions, quantities of impurities are also greater when alkaline conditions are used. Thus, there is a need for a hydrogenation process in which enhanced mannitol yield are obtained while minimizing the amounts of impurities.

U.S. Pat. No. 4,292,451 by DeBerardinis discloses a mannitol-rich aqueous solution of sorbitol and mannitol produced by hydrogenating a sugar mixture comprising glucose and mannose in aqueous solution with hydrogen in the presence of a hydrogenation catalyst under hydrogenation conditions. The sugar mixture contains an alkaline metal salt of a weak acid in sufficient quantity so that the percentage of mannitol produced exceeds the percentage of mannitol which would be obtained from hydrogenation of a sugar mixture under non-isomerization conditions. Under the above hydrogenation conditions the percent of mannitol produced is increased to about 40% as compared to about 30 to 35% in cases where no epimerization catalyst is used. Also U.S. Pat. No. 4,083,881 by Takemura et al., discloses a D-glucose solution being epimerized under the conditions of low pH and high temperatures, that is, a pH of 2.0 to 4.5 and temperature of 110° to 160° C., to produce D-mannose at a preferred level ranging from 30 to 36% as compared to 25% which is obtained by the conventional process. Takemura et al also disclose isomerization of the remaining D-glucose in the epimerized mixture of D-fructose with a glucose-isomerase enzyme. This raises the mannose yield to about 46.4% in solution and 40.3% in the crystalline form.

Various attempts have been made to reduce the cost of producing mannitol, such as U.S. Pat. No. 3,677,818 by Casebler et al. which discloses the preparation of substantially pure mannose in the form of a mannose bisulfite adducts from liquor of wood pulping operations which is rich with mannose. This, however, is a very slow process requiring several days to achieve a yield of 24% by weight of the starting material in its crystalline bisulfite adduct form. The mannose bisulfite adduct produced has to be subsequently decomposed to pure mannose in a second time consuming procedure, and the mannose produced is reduced to mannitol.

Another source for mannose is mannan from ivory nut meal which, when hydrolyzed, liberates D-mannose. However, the difficulty of extracting and recovering mannan from this complex natural source in good yield without degrading it has not been commercially feasible. Also, the availability of ivory not meal for use commercially has been limited.

It would be desirable to use mannose or fructose as starting materials to produce mannitol. However, because of the high cost of obtaining mannose or fructose in substantially pure form by the above methods, the economics of using these sugars as starting materials is not justified.

A need has arisen for a low-cost high yield mannitol process. To increase the yield according to the conventional processes would involve starting materials which are too expensive to make such production economically feasible. To satisfy the above need, it has become very desirable to identify a source of mannose or a mannan containing material which would enable easy extraction of mannose or mannan oligomers to be used as starting material for the production of mannitol or other manno-saccharide alcohols.

It has been found that a typical industrial soluble coffee process extraction residue material contains mannan and cellulose. However, its use as a source for mannose or mannan oligomers has not been disclosed. Mainly, coffee extraction residue material has been hydrolyzed to produce galactose (by hydrolyzing its arabinogalactan fraction) or hydrolyzed to produce a random mixture of sugars: galactose, xylose arabinose, mannose and glucose. The hydrolysis of coffee extraction residue material is discussed further and in more details in the following paragraphs.

The process of hydrolyzing extracted coffee grounds is well known in the art. For example, U.S. Pat. No. 2,573,406 to Clough et al. discloses a process for producing a soluble coffee which involves atmospherically extracting about 20% of the weight of the coffee, hydrolyzing a portion of the grounds in a suspension of about 1% sulfuric acid at 100° C. for about 1 hour, adjusting the pH of the hydrolysate, filtering the hydrolysate, combining the same with the atmospheric extract and drying the combined extract. In another, similar process described in U.S. Pat. No. 2,687,355 to Benner et al., phosphoric acid is used in place of sulfuric acid. Still in another process, disclosed in the U.S. Pat. No. 3,224,879 to DiNardo et al. either alkaline or acid hydrolysis is carried out directly in the extraction train of coffee grounds that have been at least atmospherically extracted. Hydrolysis directly in the extraction train eliminates separate hydrolysis step of the prior art processes and provides for adsorption of the alkaline or acid catalyst in the mass of the spent coffee grounds.

As to the Clough et al. and Brenner et al. processes, the batch hydrolysis reactions at relatively low temperatures require about 1 hour to complete, limiting the particularlity of said processes on a commercial scale. Moreover, both Clough et al. and Brenner et al. essentially aim for whatever hydrolysate results from operating at a 100° C. for 1 hour. Neither disclosure describes a method for nor the desirability of manipulating the hydrolysis condition so as to affect the composition of the resulting hydrolyzate. A similar deficiency is noted with respect to the DiNardo disclosure.

It is also widely recognized in the art that cellulosic material containing predominantly carbohydrate polymers and lignins may be hydrolyzed with an acid catalyst at high temperature short time conditions. However, if the cellulosic material is not relatively pure the hydrolysis reaction will produce undesirable by-products. For that reason, the art dealing with acid hydrolysis is of primarily cellulosic material is generally limited to the hydrolysis of waste paper and paper by-product or agricultural waste such as corn hulls, husk or cobs. For example, U.S. Pat. No. 4,201,596 to Church et al. discloses a continuous process for the saccharification of cellulosic material in a tubular reactor with an acid catalyst. The object of the Church et al. process is the conversion to glucose, furfural and xylose of cellulosic waste material such as saw dust, wood waste, corn cob, etc. Along the same line, the kinetics of the conversion of cellulosic waste to monosaccharides in a plug flow reactor are described in Thompson, David R. and Grethlein, James E. "Design Evaluation of a Plug Flow Reactor for a Acid Hydrolysis of Cellulose." Ind. Eng. Chem. Prod. Res. Dev., Vol. 18, No. 3, pp. 166 to 169 (1979). The authors of said article are specifically interested in hydrolyzing cellulose-rich material to monosaccharides essentially glucose. The authors do not disclose a method for hydrolyzing only to oligomers, much less to a specific mix of oligomers. Another disclosure, U.S. Pat. No. 4,316,747 to Rugg et al., describes a process for hydrolyzing cellulosic waste to glucose using an acid catalyst in a twin screw extruder.

Though the art discloses much about the short time high temperature acid hydrolysis cellulose-rich materials, the art does not disclose such treatment of materials in which cellulose is not the major component such as a coffee extraction residue material, particularly the spent coffee grounds from a commercial percolation system. The major hydrolyzable carbohydrate in coffee extraction residue material is mannan. However, in addition to mannan, coffee extraction residue material also contains smaller amounts of carbohydrate polymers such as cellulose and arabinogalactan. The products of mannan hydrolysis degrade under cellulose hydrolysis condition, destroying any desirable mannan oligomer intermediates that are produced.

It is therefore an object of the invention to provide a method of hydrolyzing a coffee extraction residue material to produce manno-saccharides from mannose (DP1) to about manno-decaose (DP10).

Another object of the invention is to provide a method of hydrolyzing a coffee extraction residue material to produce a manno-saccharide made up substantially of mannose.

Still another object of the invention is to neutralize and then reduce the manno-saccharides from the hydrolysis of spent coffee grounds to their corresponding alcohols.

A further object of the invention is to neutralize and reduce the mannose produced to mannitol.

Still a further object of the invention is to produce the alcohols in their powdered or crystalline form.

SUMMARY OF THE INVENTION

It has now been found that the objects of the invention are met by a process for hydrolyzing, neutralizing and subsequently reducing a coffee extraction residue material to produce sugar alcohols. This process involves slurrying the coffee extraction residue material wherein a major amount of arabinogalactan has been removed in a liquid wherein the amount of the coffee extraction residue material is between 2% and 70% by weight based on solids in the slurry; adding an acid catalyst to the slurry in an amount sufficient to adjust the pH of said slurry to between pH 0.5 to pH 5; feeding the slurry through a reactor for a time and at a temperature and pressure effective to selectively hydrolyze the mannan fraction of the coffee extraction residue material to manno-saccharides from mannose (DP1) to about manno-decaose (DP10); discharging the slurry from the reactor through an orifice so that the pressure is rapidly reduced to atmospheric; quenching the hydrolysis reaction; separating the hydrolyzed coffee extraction residue material from said manno-saccharides; and reducing said manno-saccharides for a time and at a temperature and pressure effective to produce their corresponding alcohols.

DESCRIPTION OF DRAWINGS

A feature of the present invention will become more fully apparent from the following drawing when taken in conjunction with the detail description which follows.

DETAILED DESCRIPTION OF THE INVENTION

Figure 1:
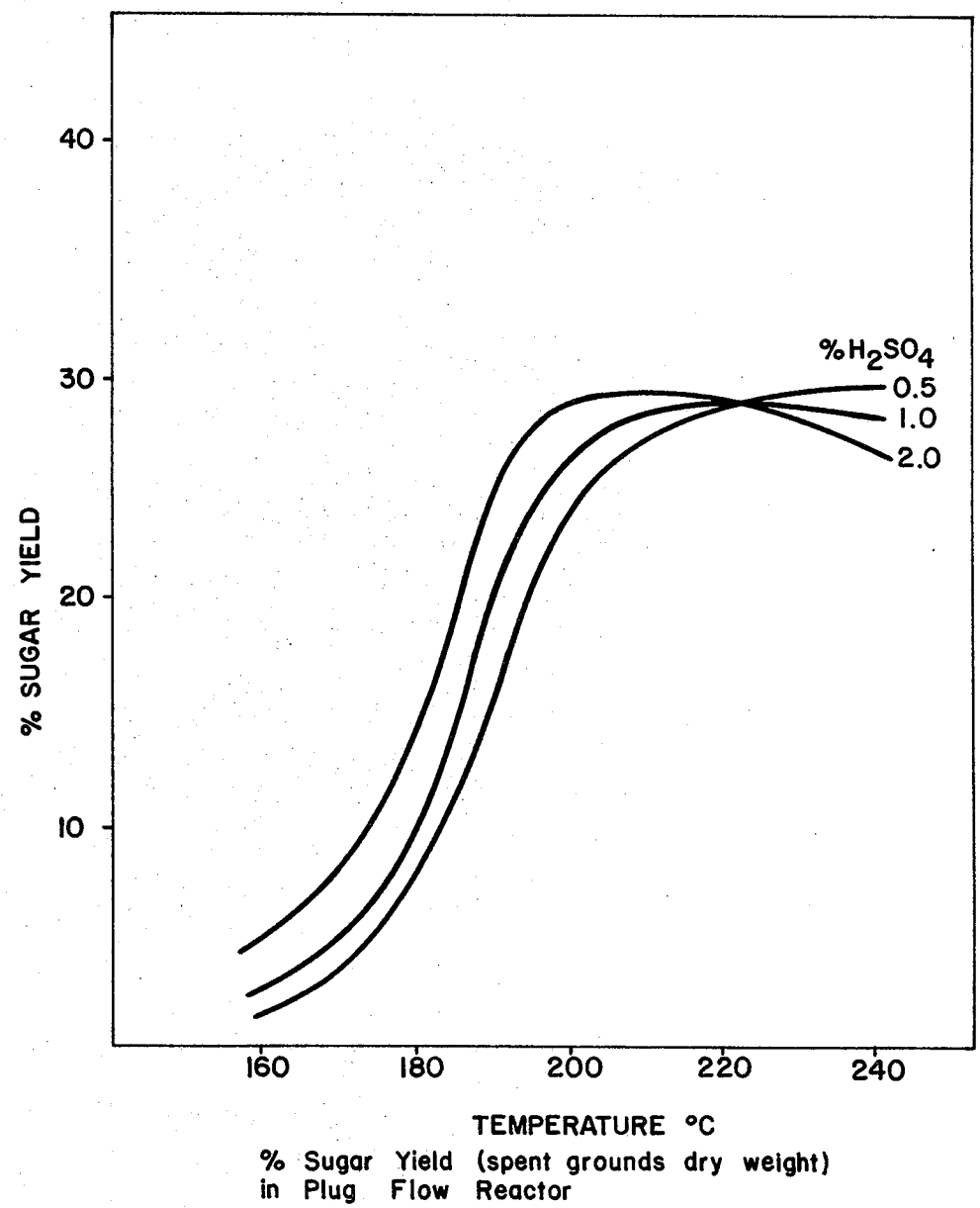
FIG. 1 is a graph showing the sugar yield versus temperature and acid level in the plug flow reactor at a residence time of about 6 seconds.

The present invention takes advantage of several properties of the coffee extraction residue material not widely recognized in the art. First, most of the art dealing with coffee grounds focuses on the cellulosic content of said grounds, not emphasizing that there is actually more mannan than cellulose present in the grounds. Moreover, the inventors herein unexpectedly found that said mannan is substantially separately hydrolyzable from the cellulose. That is to say that the conditions under which mannan and cellulose and other coffee material hydrolyze are sufficiently separated so that an essentially pure mannan hydrolysate is produced. Finally, it has been found that the mannan need not be hydrolyzed completely to a monosaccharide as is the object of most cellulose hydrolysis work [although it is possible to do so], but the mannan may be hydrolyzed to produce manno-saccharides from mannose (DP1) to about manno-decaose (DP10), which can be subsequently reduced to their corresponding alcohols without hydrogenolysis.

Before proceeding to a more detailed description of the invention, it is necessary to define some relevant terms. "Mannan" as used herein refers broadly to any polysaccharide consisting of d-mannose units. The monosaccharide d-mannose is an aldohexose and isomer of d-glucose, differing only by having the opposite steric arrangement of the hydroxyl group nearest the carbonyl. Mannan found in the coffee extraction residue material may have up to 40 d-mannose units in a polysaccharide chain, and typically is linked by beta 1–4 glycosidic linkage, identical to those found in cellulose polymer. Because coffee mannan is essentially a linear polymer with similar bonding forces to cellulose, it is also a difficult polymer to hydrolyze. However, under specific reaction conditions, the mannan fraction can be hydrolyzed without affecting the remaining cellulose fraction.

"Manno-saccharide" is intended to include mannose and manno-saccharides up to manno-decaose (DP10).

"Degree of Polymerization" or "DP" refers to the number of mono-saccharide units that make up a given manno-saccharide. Thus, a manno-saccharide of DP 4 for example consists of 4 mannose units.

Turning to the present invention; "Coffee extraction residue material" employed as the starting material is intended to mean a roast and ground coffee material that has been partially extracted. Coffee that has been partly thermally hydrolyzed in order to hydrolyze the less stable polysaccharides such as arabinogalactan is particularly useful as coffee extraction residue material. The spent grounds from a commercial percolation system is an example of coffee that has been atmospherically extracted and partly thermally hydrolyzed, such that about 35 to 60% of the starting roasted coffee grounds has been extracted, typically about 50%.

A coffee extraction residue material is usually obtained from a commercial coffee percolation system. In a typical commercial coffee percolation system, roast and ground coffee is extracted in a multi-section, countercurrent extraction battery in which fresh water at temperature in excess of about 175° C. enters the section containing most spent coffee [the coffee that has undergone the greatest extraction]. Concentrated coffee extract is withdrawn from the section containing the freshest coffee. Said coffee obviously undergoes a compositional change during percolation. Table 1 shows the approximate composition of roast and ground coffee whereas Table 2 shows the composition of spent grounds obtained from a commercial extraction system. While the overall percentage of carbohydrates remains approximately constant, the thermally hydrolyzed arabinogalactans are seen to be mostly removed. So, a preferred coffee extraction residue material is composed of about 40% to 60% by weight carbohydrates, of which about half is mannan.

TABLE 1

| Approximate Composition of Roasted Coffee | |
|---|---|
| Component | % By Weight (dry basis) |
| polymeric carbohydrates | 41 |
| arabinogalactan | 13 |
| mannan | 20 |
| cellulose | 8 |
| protein | 13 |
| caramel and browning products | 13 |
| lipids | 11 |
| inert material | 9 |
| acids | 6 |
| ash | 4 |
| caffeine | 2 |
| trigonelline | 1 |

TABLE 2

| Approximate Composition of Spent Grounds | |
|---|---|
| Component | % By Weight (dry basis) |
| polymeric carbohydrates | 45 |
| arabinogalactan | 5 |
| mannan | 25 |
| cellulose | 15 |
| lipids | 25 |
| inert material | 20 |
| protein | 10 |

According to the present invention, the coffee extraction residue material is first slurried in water or suitable liquid prior to being fed to a plug flow reactor. The slurry should be between 2% and 70% by weight solids in order to insure sufficient solid content in said reactor for efficient hydrolysis. It is preferred, however, that the slurry be between 3% and 50% by weight solids and more preferably between 4% and 15% by weight solids of the coffee extraction residue material. Moreover, the slurry should be uniform, that is, the residue material should be distributed evenly throughout. If the slurry is made up in batch beforehand, steps should be taken to insure uniformity such as recirculation by means of a slurry pump. In the event a different reactor, such as an extruder, is used, it is not necessary to dilute the spent grounds. For example, spent grounds from a conventional percolation system typically containing between about 20% and 50% by weight solids may be fed directly to such an extruder without further dilution. If desired, the spent ground can be partially dried or the water expressed to a solids level of about 70%.

An acid catalyst is then added to the slurry in order to adjust the pH to a suitable level. The acid catalyst is typically added at between about 0.1% by weight and 4.0% by weight of the slurry, preferably between about 0.1 and 2.0% by weight of the slurry. It has been found that a slurry pH between 0.5 and 5.0, and preferably between 1.0 and 3.5 is desired to catalyze the short time, high temperature hydrolysis of the coffee extraction residue material to manno-saccharides. The pH, in combination with a given reaction time, temperature, and pressure determines the distribution of the different degree of polymerization of manno-saccharides. For instance, at low pH, high temperature and a longer reaction time, mannose is produced. Conversely, a suitable combination of shorter time or lower temperature higher pH, tends to favor manno-saccharides having a higher degree of polymerization.

Specific acid catalysts contemplated for use in the present invention include both inorganic and organic acids alone or in combination. A strong inorganic acid, such as sulfuric acid is particularly suitable for use herein because of the relatively small amount of acid needed to reach the desired pH. Sulfuric acid is easy to precipitate out from the final hydrolyzate and the acid enjoys wide application in the food industry. Other inorganic acids, such as phosphoric acid, nitric acid and hydrochloric acid are also suitable as is a combination of acids such as phosphoric acid combined with sulfuric acid. Organic acids alone or in combination, such as acetic acid, citric acid, tartaric acid, malic acid, adipic acid, formic acid, and fumaric acid, succinic acid, oxalic acid and other food approved organic acids also made acceptable acid catalysts. Although being weaker, relatively greater amounts of organic acid are needed to achieve the desired pH adjustment.

After the acid catalyst has been added to the slurry, said slurry is fed to a reactor. Suitable continuous reactors include those capable of promoting relatively high temperature, short time reactions, such as single or double screw extruders or plug flow tubular reactors. A suitable batch reactor is a so-called explosion puffer wherein the coffee extraction residue material is mixed with the acid catalyst, placed in the reactor vessel which is then pressurized, as with steam. The pressure is suddenly and explosively released, discharging the contents from the reaction vessel. The manno-saccharides, preferably mannose is leached from the material so discharged from said reaction vessel. The plug flow tubular reactors are especially convenient. A plug flow tubular reactor is essentially a cylindrical length of pipe in which a reaction can take place. An orifice is placed on the discharge end of the reactor in order to control the pressure in the reactor as well as the rate of discharge from said reactor. "Plug flow" refers to the velocity profile of the slurry flowing through the reactor. Normally, a fluid exhibits a parabolic velocity profile wherein the fluid in the center of a conduit has a higher velocity than fluid flowing closer to the wall. In a plug flow reactor, the velocity profile is flat, arising from the geometry of the vessel and the nature of the fluid.

The elevated temperature is achieved in the reactor by any of several ways. For example, the slurry may be passed through a heat exchanger prior to entering said reactor. Temperature may then be maintained by simply insulating the reactor. Alternatively, high pressure steam may be injected directly into the reactor as a means of increasing the temperature. Although the steam may dilute the slurry somewhat, such heating is extremely rapid, permitting short time reactions. Selection of a preferred heating method, as well as sizing of the diameter of the reactor and orifice are all within the skill of a worker in the art, based on standard design principles.

The conditions within the reactor are, of course, critical in insuring that essentially only mannan is hydrolyzed and that the desired distribution of manno-saccharides is produced. In the case of mannose, the conditions in the reactor are adjusted so that mannan is hydrolyzed completely to mannose. It has been found that the reaction temperatures should be between 160° C. and 240° C., preferably from 180° C. to 220° C., in order the hydrolyze the mannan and minimize the degradation of manno-saccharides so produced. Such temperatures correspond generally to a pressure in said reactor between 130 psig and 700 psig, which is slightly above the saturation pressure of the water in the slurry fed through the reactor at the above condition. However, the pressure in the reactor can range from about 75 psig to about 2000 psig. In general, a higher temperature promotes the production of manno-saccharides of a lower degree of polymerization such as mannose (depending on the pH and the length of reaction) and the converse is also generally true.

The preferred reaction time has been found to be between 6 seconds and 300 seconds, preferably 6 seconds to about 60 seconds. Below about 6 seconds, the equipment is limiting as it is very difficult to heat the slurry and insure uniformity of the reaction. On the other hand, if the reaction is carried out for much longer time using a stronger acid catalyst, the mannose in the hydrolysate begins to degrade, causing off flavors, limiting the useful yield and making purification of the hydrolysate difficult.

As hereinbefore noted, the discharge end of the reactor has an orifice thereon to control pressure within the reactor and control the rate of discharge. Passing the slurry through the orifice rapidly reduces the pressure to which the slurry is subjected to about atmospheric. Such a rapid reduction of pressure causes expansion and evaporative cooling of the slurry thereby "quenching" or effectively terminating the hydrolysis reaction. By so quenching the reaction, it is possible to control the reaction time to within the prescribed 6 seconds to 60 seconds with great reliability.

Once the slurry is discharged from the plug flow tubular reactor, said slurry is cooled further. The solution that is produced is made up substantially of manno-saccharides and the remaining hydrolyzed coffee extraction residue material. It is possible to neutralize the discharged slurry by known techniques, such as precipitation of the acid with a salt, evaporation of the volatile acid or the use of an ion exchange resin. The neutralization may be either before or after the separation of the manno-saccharides and the hydrolyzed coffee extraction residue material. Separation may be by any method of solid-liquid separation known in the art. For example, said slurry may be filtered in order to remove the hydrolyzed coffee extraction material therefrom. Alternatively, the slurry may be separated by centrifuging the slurry as in a basket centrifuge. After separation, the hydrolyzed coffee extraction residue material is disposed of, most preferably burned for fuel.

According to the present invention, the mixture of manno-saccharides from DP1 to about DP10 separated from the hydrolyzed coffee extraction residue material is neutralized. The neutralization is accomplished by the addition of a base, an alkali metal salt or an alkaline earth metal salt. Calcium hydroxide or lime are preferred neutralizing agents. Other water-soluble or dispersable neutralizing agents are calcium carbonate, sodium carbonate, sodium bicarbonate, sodium hydroxide, potassium hydroxide, potassium carbonate and potassium bicarbonate may also be used. The neutralizing agent may be added to the solution either before or after the separation of the mannose produced from the hydrolyzed coffee extraction residue material.

The amount of calcium hydroxide or lime added to the acidified hydrolysate should be sufficient to raise the pH to between about pH 3 and pH 8 and preferably between about pH 5 and pH 7.

It is also possible to separate the acid from the hydrolyzed manno-saccharide by electro-dialysis, ion exchange, evaporation or other known means.

The neutralized manno-saccharides are then converted to their corresponding alcohols, which ranges from mannitol to manno-decitol. This conversion is accomplished by a reduction process. In this process the reduction to alcohols is achieved preferably by catalytic hydrogenation or other procedures either by a batch or a continuous process. In one embodiment, reduction is accomplished by hydrogenating the manno-saccharides for a time and at a temperature and pressure effective to reduce the aldehyde groups to alcohols ranging from mannitol to manno-decitol. Hydrogenation according to this invention is carried out at temperatures from between about 100° C. to about 160° C., preferably at temperatures from about 120° C. to about 150° C. Hydrogenation can be carried out at relatively low temperatures for a long period of time or relatively high temperatures for a shorter time period. The reaction time for hydrogenating the manno-saccharides at the above temperatures ranges from about 0.3 to about 8.0 hours. It is preferred, however, that the reaction time be between about 0.5 hours and 2.0 hours. The reaction time required to hydrogenate the manno-saccharides depends primarily on the reaction temperature. An increase in temperature results in a reduction in the reaction time required.

The pressure in the reaction vessel can vary widely. However, elevated pressures from about 500 psig to about 2000 psig can be used, with pressures between about 1200 psig to about 2000 psig being preferred.

The hydrogenation according to the present invention is conducted in the presence of a catalyst and under effective conditions whereby the time of subjecting to elevated temperatures and pressure is minimized. It has been found satisfactory to add supported Nickel to the neutralized manno-saccharides wherein the supported Nickel acts as catalyst thereby driving the reaction to completion at a more rapid rate. The required amount of supported Nickel needed as a catalyst ranges from 0.3% to 8.0% by weight of the neutralized manno-saccharides syrup and will usually be sufficient. Preferably, supported Nickel content should range from about 0.51% to about 4.0% based on the weight of the manno-saccharides. Types of supported nickel catalysts are Nickel supported on Kieselguhr and Nickel Supported on diatomaceous earth. Other catalysts such as Raney Nickel and Ruthenium supported on alumino silicate clay and platinum group catalyst such as platinum or palladium are also satisfactory.

Hydrogenation can be carried out in any suitable type of apparatus which enables the reaction to be carried out and wherein the operating conditions can be controlled. This apparatus must be able to withstand elevated pressure conditions. Also, an apparatus such as a pipe containing the supported catalyst through which the manno-saccharides and hydrogen gas can be cycled and which allows for continuous operation is preferred. An autoclave is a suitable apparatus for carrying out the present invention because of its ability of maintain high temperatures and pressure conditions.

An alternative embodiment for hydrogenating the manno-saccharides to their corresponding alcohols or mannose to mannitol is the electrolytic reduction process for reducing sugars to alcohols. This process for reduction and apparatus employed is disclosed in U.S. Pat. No. 2,300,218 by Hales. In accordance with the present invention, the Hales process discloses the reduction of sugar to a polyhydric alcohol while maintaining the main body of the catholyte in acid condition, provided the acid catholyte contains an alkali metal sulfate. During electrolysis, such a catholyte is made alkaline in the region immediately surrounding the cathode so that reduction is made possible even though the main body of the catholyte is acidic. There is a continuous formation of a thin film or layer of alkaline catholyte around the cathode. The alkaline conditions thus brought about at the cathode cause transformation of the saccharide to a form in which it is reducible to a polyhydric alcohol by the action of the nascent hydrogen liberated at the cathode. In the present invention this occurs at a pH of between 2.3 and 7.

Another alternative embodiment of the present invention is the chemical reduction of manno-saccharides to their corresponding alcohols or in the case of mannose to mannitol. In this process sodium borohydride ($NaBH_4$) decomposes to produce hydrogen and sodium borate. The hydrogen so produced reduces the sugar aldehyde to the alcohol form.

The electrolytic reduction though practical and gives the desired alcohols, has severe economic drawbacks. That is, it is a very costly process, resulting in it being less preferred. The chemical and thermal reductions are also effective and produce comparable results. However, the thermal catalytic process is most cost-effective commercially.

The alcohols produced, that is, alcohols ranging from mannitol to manno-decitol can be used as a liquid or can be dried by known techniques such as spray drying, freeze drying, air drying etc., to a powder and in the case of mannitol crystallize to form alcohol crystals.

Mannitol, the preferred alcohol of the present invention, a sugar alcohol, is an expensive specialty food, chemical and pharmaceutical ingredient. Mannitol has a sweetness about 60% that of sucrose and is of relatively low hydroscopicity in its crystalline form. For these reasons, mannitol is being used in the manufacture of sugar-less chewing gum, dietetic candies, and as a weight reduction aid. Mannitol is also presently used as a fixative for acetaldehyde.

Mannitol also has a variety of uses in the pharmaceutical industry which include a base in chewable, multi-layered and processed coated tablets for vitamins, antacids, aspirins, and other products because of its low affinity for water; good tablet disintegration properties and its ability to mask the unpleasant taste of the drugs. Mannitol is also used in the manufacture of synthetic resins, plasticizers, and as the drug mannitol hexanitrate which acts as a vasodilator. Mannitol is combined with boric acid in the manufacture of dry electrolytic condensers as an electronics application. Thus, mannitol has a broad commercial market.

The mixture of alcohols ranging from mannitol to manno-decitol can be used as encapsulants for flavors and pharmaceuticals or as non-cariogenic mixtures in foods and confectionaries.

The following examples illustrate certain embodiments of the present invention. The examples are not to limit the invention beyond what is claimed below.

EXAMPLE 1

A hydrolysate was prepared by acid hydrolysis of spent coffee grounds which resulted from a commercial percolation process in which a soluble coffee yield of about 50% (basis starting roast and ground coffee) was achieved. The spent grounds had a 56.3% moisture. Two hundred grams of these grounds were added to about 1600 grams of water and blended in a large Waring blender at high speed for 3 to 5 min. The mixture was transferred to Gifford Wood colloid mill (model W-200) and passed through the mill at 40 setting and in successive passes the setting was reduced to 15. About 30 batches of 1800 ml slurry were prepared. The slurry having particles below 0.8 mm had a concentration of about 5% solids (wt/volume).

The plug flow reactor system consisted of:
1. a slurry tank with stirrer
2. a Moyno pump
3. a high pressure steam boiler
4. a pump to inject acid into the slurry
5. a reactor tube with orifice
6. a water cooled condenser The spent grounds slurry was pumped (via Moyno pump) from the slurry tank to the reactor where it was rapidly heated to 190° C. by adjusting the steam boiler to 380 psig and a valve to reduce the steam entering the reactor to 190 psig. One percent sulfuric acid was injected into the slurry just prior to heating to the desired reaction temperature. The residence time of the slurry in the reactor was 8.1 sec. The reaction was then quenched by flashing the hydrolysate back to atmospheric pressure as it exited the 0.8 mm orifice. The hydrolysate had a pH of 1.0. The mixture discharge from the reactor was cooled to about 30° C. then the hydrolysate was separated from the coffee extraction residue material. The hydrolysate was then neutralized with calcium carbonate to a pH of about 6 and filtered through a Buchner funnel. The hydrolysate had a clear amber color. Under these conditions 24.6% of the grounds were solubilized (d.b.) and based upon analysis by high pressure liquid chromatography 19.5% of grounds were converted to sugars.

| Sugar Composition of Hydrolysate | | |
|---|---|---|
| | Relative % Sugar | Sugar Yield % of Spent Grounds (d.b.) |
| Cellobiose | 0.32% | 0.06% |
| Glucose | 2.30% | 0.45% |
| Xylose | 1.07% | 0.21% |
| Galactose | 1.30% | 0.25% |
| Mannose | 95.00% | 18.51% |
| TOTAL | 99.99% | 19.48% |

The starting spent grounds were quantitively saccharified by known procedure to determine the amount of glucose and mannose that would be available upon hydrolysis. It was found that the starting spent grounds could maximally yield 16.9% glucose and 26.07% mannose. This indicated that about 3% cellulose and 71% mannose was solubilized in this example.

Two hundred ml of the above hydrolysate having an identified sugar composition of 0.72% ± 0.07% total sugars or 0.71 ±0.07% mannose were placed in a three necked flask. Nitrogen was bubbled in one neck and pH was monitored in the other neck. The starting pH was brought to 8.0 with sodium hydroxide.

Slowly, while stirring, 1.0 g sodium borohydride was added in small aliquots. Stirring was continued for 1 hr. Carbon dioxide gas was bubbled in occasionally to keep the reaction mixture near pH 9.00. The pH ranged between 8.7 and 9.3.

After 1 hour the reaction mixture was slurried with 50W-X-8 cation exchange resin until the pH drops to 3.5 (converts sodium borate to boric acid). The resin was filtered off and the solution evaporated under vacuum (Rotovap-Buchli) to almost complete dryness at 46° C. Fifty ml of methanol were added to the mixture and the mixture evaporated to dryness five times. This converts the boric acid to methyborate ester which is removed by distillation. White crystals were evident. The crystals were rinsed with ethanol three times to remove the light brown color. The sample weight was about 1.61 gms. An aliquot of the sample was acetylated and analyzed by gas chromatography to be 97.5% ±10% mannitol. The overall accuracy of this experiment was ±10%. However, the results indicated that the mannitol was qualitatively produced and was of high purity.

EXAMPLE 2

In a designed experiment, the conditions of hydrolysis of the spent grounds in the plug flow reactor were varied. The procedures for running the plug flow reactor, neutralization and filtration were kept the same as example 1.

Temperatures examined: 160° C., 180° C., 200° C., 240° C.

Sulfuric acid levels examined: 0.5%, 1.0%, 2.0%

Residence time range: 6.7–8.7 sec.

The following results show optimization conditions for producing mannitol by varying the temperature and acid concentration.

Figure 2:
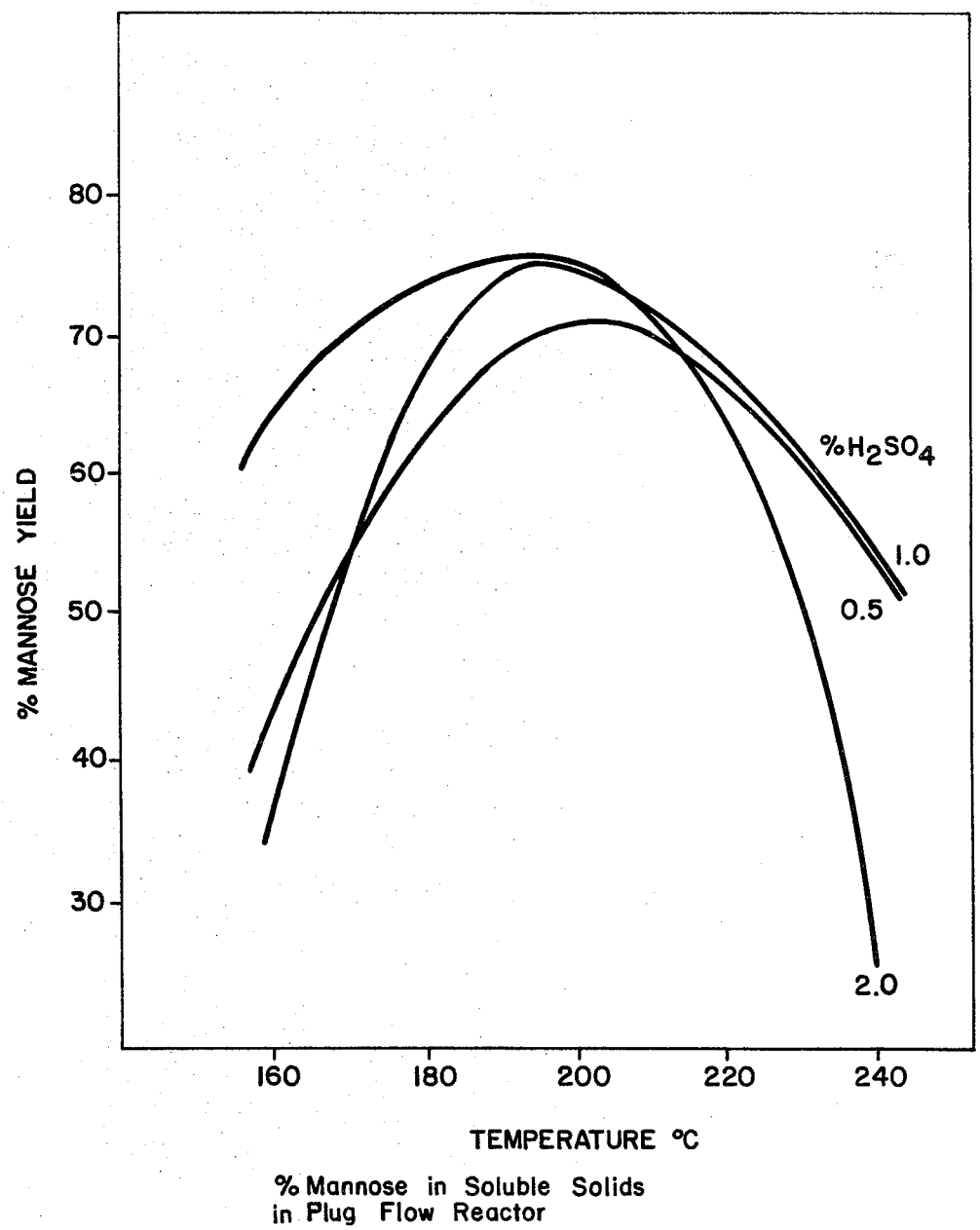
FIG. 2 is a graph showing the % mannose in soluble solids versus temperature and acid level in the plug flow reactor at a residence time of about 6 seconds.
Figure 3:
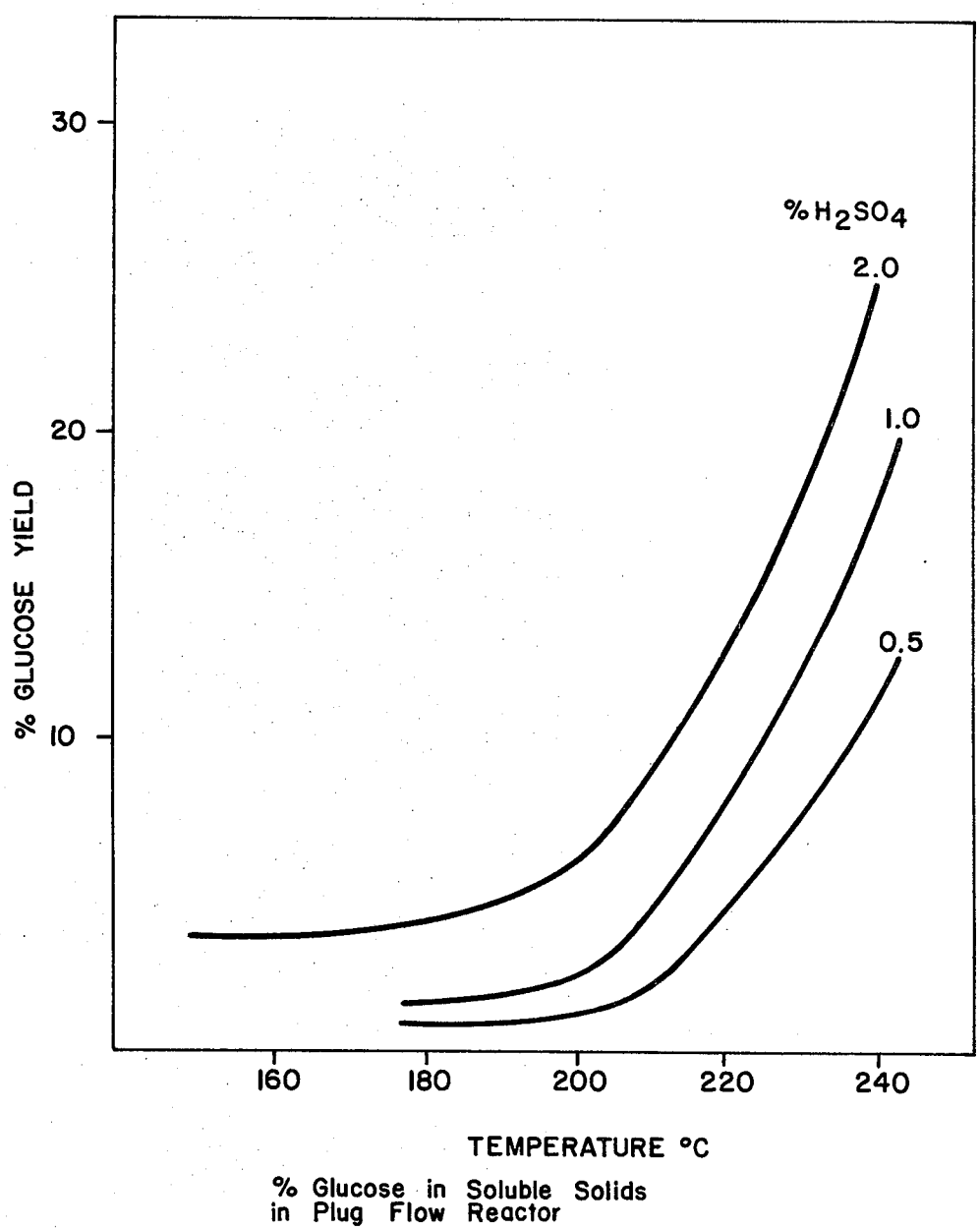
FIG. 3 is a graph showing the % glucose in soluble solids versus temperature and acid level in the plug flow reactor at a residence time of about 6 seconds.

The sugar yield was observed to increase between 160° C. and 200° C. and level off about 200° C. At the 2% acid level the sugar yield decreased due to decomposition (FIG. 1) above 200° C. The percent of mannose in the solubilized solids were observed to increase between 160° C. and 200° C. and decrease markedly above 200° C. (FIG. 2) indicating that the mannan fraction was hydrolyzed in this temperature range. The percent of glucose in the hydrolyzed solids, an indication of cellulose hydrolysis, did not increase markedly until above 200° C. (FIG. 3). The data indicated that mannan fraction could be hydrolyzed selectively from the cellulose fraction in the range of 190 to 210° C. and a mannose yield of about 25% of the spent grounds (d.b.) could be obtained.

After neutralization with calcium carbonate and filtration the hydrolysate was concentrated to 10–30% solids by evaporative means, and was deionized by passing through a cation exchange resin (e.g. Amberlite IR-120 in the hydrogen form) and an anion exchange resin in the free base form (e.g. Amberlite IR-95). The process not only removes trace calcium sulfate but also removes much of the caramel color in the hydrolysate.

The mannose rich hydrolysate was then reduced to mannitol in a manner consistent with Example I.

The hydrolysate can also be reduced electrolytically in sulfuric acid solution by the procedure of R. Hales (U.S. Pat. No. 2,300,218). In our case, the hydrolysate is brought to pH 2.0 with sodium hydroxide and concentrated to about 20% sugar solids under vacuum and supplemented with enough sodium sulfate to bring the solution to about a level of 80 grams per liter. The hydrolysate (catholyte) is electrolytically reduced at an amalgamated zinc cathode at 70° F. and at a current density of about 1 amp. per sq. dm. for a period of about 100 hours. The reduced hydrolysate is then concentrated to about 60% solids and cooled to about 10° C. where white crystals of mannitol are formed. The mannitol is separated by filtration and redissolved in water at about 50% concentration, deionized, and recrystalized.

EXAMPLE 3

A series of runs was conducted using essentially the same procedure but varying the acid catalyst, the reaction temperature and the reaction time. The procedure was as follows:

Spent coffee grounds from a commercial percolation process were dispersed in water and milled using a Gifford Wood W-200 Colloid Mill to a particle size below 0.8 mm (the orifice size of plug flow reactor) to give a slurry of 4.68% by weight solids. The slurry was then placed in the hopper of a plug flow reactor at room temperature and kept agitated to prevent settling. The slurry was then pumped using a Moyno pump into the plug flow reactor having about 113 ml volume. Just prior to feeding the slurry into the reactor, a previously calibrated quantity of 94% by weight sulphuric acid was pumped into the slurry stream with a small variable stroke piston pump to give the desired acid concentration. The reactor consisted of a heating section in which steam was injected directly into the slurry and a reaction section which was essentially a length of tubing. After the slurry entered said reactor, the temperature was rapidly raised by condensation of steam injected into the slurry. The temperature of the reactor was changed by varying the steam pressure by means of a valve and was monitored with a thermocouple. Residence time of the slurry in the reactor could be varied by changing the pumping speed of the Moyno pump. After passing from the reactor through the orifice of the reactor, the slurry dropped back to atmospheric pressure and the temperature correspondingly dropped to about 100° C., quenching the reaction. The slurry and any condensate were further cooled to about room temperature by passing the same through a water cooled heat exchanger. The hydrolyzed slurry was then neutralized with calcium carbonate, and the residue was filtered therefrom.

The resulting hydrolysate containing the manno-saccharide mixture was analyzed to determine both composition and the distribution of the manno-saccharides between about DP 1 and DP 10. The purity of the manno-saccharide mixtures were typically in excess of 80%, indicating that essentially only the mannan and very little cellulose was hydrolyzed.

High performance liquid chromatography (H.P.L.C.) was used for the analysis, with the percentage indicated being the relative percentage of the total peak area for the manno-saccharides. The analysis was carried out on a Waters Carbohydrate Analysis column (part number 84038) with a solvent of 70/30 acetonitrile/water. The analysis was run at ambient temperature (20-25° C.), with a solvent flow rate of about 2 ml/min. The peaks were monitored with a Waters differential refractive index detector.

Table 4 shows the results for sulphuric acid. Table 5 shows the results for phosphoric acid and Table 6 shows the results for acetic acid.

TABLE 4

Sulphuric Acid Catalyst

| acid catalyst level % weight | temp. °C. | time sec | Distribution of manno-saccharides (%) by area | | | | | | | | |
|---|---|---|---|---|---|---|---|---|---|---|---|
| | | | DP1 | DP2 | DP3 | DP4 | DP5 | DP6 | DP7 | DP8 | DP9 |
| 0.25 | 200 | 8 | 51.9 | 20.9 | 13.5 | 8.3 | 2.6 | 1.4 | 0.7 | 0.7 | — |
| 0.10 | 220 | 8 | 36.3 | 23.0 | 15.4 | 10.2 | 6.7 | 4.3 | 2.7 | 1.3 | — |
| 0.05 | 220 | 8 | 14.5 | 15.8 | 15.7 | 14.3 | 13.1 | 11.5 | 8.2 | 4.8 | 2.1 |
| 0.025 | 240 | 8 | 12.6 | 14.0 | 14.9 | 14.7 | 14.3 | 12.7 | 8.9 | 4.7 | 3.3 |

TABLE 5

Phosphoric Acid Catalyst

| acid catalyst level % weight | temp. °C. | time sec | Distribution of manno-saccharides (%) by area | | | | | | | | |
|---|---|---|---|---|---|---|---|---|---|---|---|
| | | | DP1 | DP2 | DP3 | DP4 | DP5 | DP6 | DP7 | DP8 | DP9 |
| 0.25 | 240 | 30 | 100 | — | — | — | — | — | — | — | — |
| 0.25 | 220 | 30 | 58.2 | 22.7 | 11.8 | 4.4 | 2.0 | 0.9 | — | — | — |
| 0.25 | 200 | 30 | 25.4 | 21.7 | 17.4 | 13.0 | 9.8 | 6.5 | 4.0 | 2.3 | — |
| 0.25 | 180 | 30 | 22.3 | 20.6 | 15.3 | 12.8 | 13.4 | 10.0 | 4.7 | — | — |
| 1.0 | 200 | 30 | 68.8 | 15.6 | 6.8 | 5.2 | 2.1 | 1.6 | 1.9 | — | — |

TABLE 6

Acetic Acid Catalyst

| acid catalyst level % weight | temp. °C. | time sec | Distribution of manno-saccharides (%) by area | | | | | | | | |
|---|---|---|---|---|---|---|---|---|---|---|---|
| | | | DP1 | DP2 | DP3 | DP4 | DP5 | DP6 | DP7 | DP8 | DP9 |
| 1.0 | 220 | 30 | 14.3 | 15.1 | 15.0 | 15.0 | 14.6 | 12.1 | 8.5 | 5.5 | — |
| 1.0 | 200 | 30 | 12.6 | 13.5 | 11.2 | 12.2 | 13.6 | 15.4 | 9.1 | 12.3 | — |
| 0.25 | 240 | 30 | 14.0 | 15.0 | 15.2 | 14.9 | 13.1 | 12.4 | 9.1 | 6.4 | — |
| 0.25 | 220 | 30 | 14.2 | 12.8 | 13.6 | 14.0 | 13.5 | 13.7 | 11.0 | 2.1 | — |

TABLE 6-continued

Acetic Acid Catalyst

| acid catalyst level % weight | temp. °C. | time sec | Distribution of manno-saccharides (%) by area | | | | | | | | |
|---|---|---|---|---|---|---|---|---|---|---|---|
| | | | DP1 | DP2 | DP3 | DP4 | DP5 | DP6 | DP7 | DP8 | DP9 |
| 0.25 | 200 | 30 | 23.0 | 12.6 | 11.2 | 12.2 | 13.6 | 15.4 | 9.1 | 12.3 | — |

Examination of the above tables indicates that varying distribution of the manno-saccharides are obtainable by varying the acid catalyst, the reaction temperature and the reaction time. The general trend is for oligomers of lower degree of polymerization for increasing acid concentration, increasing temperature and increasing reaction time.

As previously described, the manno-saccharides can be reduced to alcohols in a manner consistent with Examples I and II.

The hydrolysate can also be reduced by known catalytic means to alcohols. In this process, two hundred grams of the above hydrolysate at 50% concentration at pH 6.5 and 4.0 grams of a nickel catalyst supported on kieselguhr are placed in an autoclave. The autoclave is flushed with nitrogen and pressurized to 1700 psig with hydrogen and heated to 150° C. for 1 hour. After this period the autoclave is cooled to about 60° C., depressurized, and the catalyst removed by filtration at 60° C. The filtrate at 60° C. is treated with anionic and cationic exchange resin and with carbon and concentrated to about 60% solids and dried.

What is claimed is:

1. A process for preparing manno-saccharide alcohols from coffee extraction residue material comprising the steps of:
   (a) slurrying the coffee extraction residue material wherein a major amount of the arabinogalactan has been removed in an aqueous medium wherein the amount of the coffee extraction residue material is between 2% and 70% by weight based on solids in the slurry;
   (b) adding an acid catalyst to the slurry in an amount sufficient to adjust the pH of said slurry to between pH 0.5 and to pH 5;
   (c) feeding the slurry through a reactor for a time and at a temperature and pressure effective to selectively hydrolyze the mannan fraction of the coffee extraction residue material to manno-saccharides from mannose (DP 1) to about manno-decaose (DP 10);
   (d) discharging the slurry from the reactor through an orifice so that the pressure is rapidly reduced to atmospheric, and quenching the hydrolysis reaction;
   (e) separating the hydrolyzed coffee extraction residue material from said manno-saccharides;
   (f) reducing said separated manno-saccharides for a time and at a temperature and pressure effective to produce their corresponding alcohols.

2. A process according to claim 1 wherein the slurry is between about 3% to about 50% by weight dry basis, coffee extraction residue material.

3. A process according to claim 2 wherein the slurry is more preferably between about 4% to about 15% by weight basis, coffee extraction residue material.

4. A process according to claim 1 wherein the reactor is a plug flow tubular reactor.

5. A process according to claim 1 wherein the coffee extraction residue material is composed of coffee grounds that have been atmospherically extracted and then thermally hydrolyzed to remove essentially all of the arabinogalactan therefrom.

6. A process according to claim 1 wherein the acid catalyst is selected from a group comprising sulphuric acid, phosphoric acid, nitric acid, hydrochloric acid, acetic acid, citric acid, tartaric acid, malic acid, adipic acid, fumaric acid, formic acid succinic acid, oxalic acid and combinations thereof.

7. A process according to claim 6 wherein the catalyst is sulphuric acid.

8. A process according to claim 6 wherein sulfuric acid is added to the slurry in amounts ranging from 0.1% to about 4% by weight of said slurry as a catalyst.

9. A process according to claim 8 wherein the sulfuric acid is added to the slurry in amounts ranging from 0.1% to about 2% by weight of said slurry as a catalyst.

10. A process according to claim 4 wherein the temperature in the plug flow tubular reactor is from 160° C. to 240° C.

11. A process according to claim 10 wherein the temperature in the plug flow tubular reactor is from 180° C. to 220° C.

12. A process according to claim 1 wherein the residence time in the plug flow tubular reactor ranges from about between 6 seconds and 300 seconds.

13. A process according to claim 12 wherein the residence time in the plug flow tubular reactor ranges from about between 6 seconds to 60 seconds.

14. A process according to claim 1 wherein the pressure in the plug flow tubular reactor ranges from between about 75 psig to about 2000 psig.

15. A process according to claim 1 wherein the pressure in the plug flow tubular reactor ranges from between about 130 and 700 psig.

16. A process according to claim 1 wherein the manno-saccharides produced are neutralized with a member selected from a group comprising calcium carbonate, calcium hydroxide, calcium oxide, sodium hydroxide, potassium hydroxide, potassium carbonate, potassium bicarbonate, sodium bicarbonate, sodium carbonate or combinations thereof.

17. A process according to claim 16 wherein the neutralizing agent is calcium hydroxide.

18. A process according to claim 1 wherein the manno-saccharides having a degree of polmerization from 1 to 10 is reduced to their corresponding alcohol in a pressure vessel in the presence of a catalyst.

19. A process according to claim 18 wherein the reaction catalyst is selected from a group comprising Raney Nickel, Nickel supported on Kieselguhr, Nickel supported on diatomaecous earth, and Ruthenium supported on alumino silicate clay, platinum group catalyst (platinum or palladium) or combinations thereof.

20. A process according to claim 19 wherein a preferred catalyst is a supported Nickel catalyst.

21. A process according to claim 18 wherein the reaction temperature ranges from about between 100° C. and about 160° C.

22. A process according to claim 21 wherein the reaction temperature ranges from about between 120° C. and about 150° C.

23. A process according to claim 17 wherein the reaction pressure ranges from about between 500 psig and about 2000 psig.

24. A process according to claim 22 wherein the reaction pressure ranges from about 1,200 psig to about 2,000 psig.

25. A process according to claim 17 wherein the processing time ranges from about between 0.3 hour and 8 hours.

26. A process according to claim 25 wherein the process time ranges from between about ½ hour and 2 hours.

27. A process according to claim 20 wherein the supported Nickel catalyst is added to the manno-saccharides at between 0.3% and 8.0% by weight of the neutralized manno-saccharides as a catalyst.

28. A process according to claim 27 wherein the levels of supported Nickel catalyst added is between about 0.5% and 4%.

29. A process according to claim 1 wherein the manno-saccharides produced are reduced to a mixture of their corresponding alcohols electrolytically.

30. A process according to claim 29 wherein the electrolytic reduction occurs at a pH of between about 2.3 and 7.

31. A process according to claim 1 wherein the manno-saccharides are reduced to a mixture of their corresponding alcohol chemically.

32. A process according to claim 1 wherein the sugar produced upon hydrolysis is substantially mannose.

33. A process according to claim 1 wherein the alcohols produced ranges from mannitol to manno-decitol.

34. A process according to claim 33 where the alcohol produced is mannitol.

35. A process according to claim 1 comprising an additional step of drying the alcohols.

36. A process according to claim 1 comprising an additional step of crystalizing the mannitol.

37. A process according to claim 1b wherein the acid catalyst is added to the slurry in amounts sufficient to adjust the pH of the slurry to between pH 1 and pH 3.5.

38. A process according to claim 1 comprising an additional step of adjusting the pH of the manno-saccharide hydrolysate to a pH of between about pH 3 and pH 8.

39. A process according to claim 37 wherein the pH of the manno-saccharide hydrolysate is adjusted to a pH of between about pH 5 and pH 7.

* * * * *